United States Patent [19]
Mitha et al.

[11] Patent Number: 6,026,829
[45] Date of Patent: Feb. 22, 2000

[54] DENTAL FLOSS CONTAINING ENCAPSULATING FLAVORING MATERIAL

[75] Inventors: Amin Mitha, San Jose; Dave Anglin, Santa Clara, both of Calif.

[73] Assignee: Gillette Canada Inc., Kirkland, Canada

[21] Appl. No.: 08/877,481

[22] Filed: Jun. 17, 1997

[51] Int. Cl.⁷ .................................................. A61C 15/00
[52] U.S. Cl. .......................................................... 132/321
[58] Field of Search ..................................... 132/321, 329

[56] References Cited

U.S. PATENT DOCUMENTS

| | | | |
|---|---|---|---|
| 3,771,536 | 11/1973 | Dragan . | |
| 3,830,246 | 8/1974 | Gillings . | |
| 3,902,509 | 9/1975 | Tundermann et al. | 132/321 |
| 3,943,949 | 3/1976 | Ashton et al. | 132/321 |
| 3,957,964 | 5/1976 | Grimm, III . | |
| 4,033,365 | 7/1977 | Klepak et al. | 132/321 |
| 4,414,990 | 11/1983 | Yost . | |
| 4,515,769 | 5/1985 | Merritt et al. . | |
| 4,568,560 | 2/1986 | Schobel . | |
| 4,980,154 | 12/1990 | Gordon . | |
| 4,986,288 | 1/1991 | Kent et al. | 132/321 |
| 5,004,595 | 4/1991 | Cherukuri et al. . | |
| 5,226,434 | 7/1993 | Britton et al. | 132/321 |
| 5,226,435 | 7/1993 | Suhonen et al. | 132/321 |
| 5,284,169 | 2/1994 | Gilligan et al. | 132/321 |
| 5,353,820 | 10/1994 | Suhonen et al. | 132/321 |
| 5,357,990 | 10/1994 | Suhonen et al. | 132/321 |
| 5,423,337 | 6/1995 | Ahlert et al. | 132/321 |
| 5,503,842 | 4/1996 | Fazan et al. | 424/443 |
| 5,505,216 | 4/1996 | Gilligan et al. | 132/321 |

*Primary Examiner*—Todd E. Manahan
*Attorney, Agent, or Firm*—Chester Cekala

[57] ABSTRACT

A dental floss is provided comprising a plurality of filaments of a substrate material formed into thread, an ingestible binder on the filaments which are bound to particles of encapsulated agents. The encapsulated agents are flavorants, sweeteners and chemotherapeutic agents. The encapsulation of the agents provides a uniform taste and distribution of chemotherapeutic agent on the floss.

16 Claims, No Drawings

DENTAL FLOSS CONTAINING ENCAPSULATING FLAVORING MATERIAL

The invention relates to articles for cleaning the interproximal spaces and surfaces of the teeth and more particularly to flavored dental floss and dental tape.

To supplement brushing of the teeth, various materials have been used such as dental floss and dental tape. It is to be understood that the term dental floss encompasses dental tape as well as a similar article used for cleaning the interproximal spaces and surfaces of the teeth.

The use of flavored dental floss makes the use of the floss more pleasant, which encourages better hygiene practices. Typical flavorants are such materials as mint or spearmint but, if used alone, they can result in an unpleasant aftertaste. Accordingly, in addition to the flavoring oils, the yarn used for making the floss is also dipped or rolled in a sweetening agent such as saccharin. Chemotherapeutic agents such as sodium fluoride are also added to a coating or impregnated in the floss to enhance the oral hygiene effectiveness.

However since the flavoring oils, sweetener and chemotherapeutic agent have different volatilities, solubilities and shelf-life, it is often difficult to uniformly incorporate these materials onto the floss or to retain the shelf-life efficacy of one or more of these materials.

SUMMARY OF THE INVENTION

The invention provides the dental floss comprising a plurality of filaments of a substrate material formed into a thread, ingestible binder on the filaments which binds particles of encapsulated agents. The encapsulated agents comprise and flavorant and a sweetening agent to provide uniform taste on the floss. A chemotherapeutic agent such as sodium fluoride or stannous fluoride may also be incorporated into the encapsulated particle.

DESCRIPTION OF THE PREFERRED EMBODIMENTS

Dental floss according to the invention will comprise a plurality of filaments of a substrate material formed into a thread. The substrate material may be nylon, gel, or any other material which may be braided or twisted to form a thread.

The floss will be coated or impregnated with an ingestible binder which may be a polymer, wax or an adhesive. The particles containing the flavorants, sweeteners and therapeutic agents adhere to the exposed surfaces of the floss, which makes their effect more efficient compared to being impregnated within and between the threads of the floss. Exemplary polymers include, but are not limited to, aqueous based polymers such as alkylene-vinyl co-polymers (e.g., Vinnapas, an ethylene vinyl co-polymer manufactured by Air Products) or acrylic emulsions (e.g., Roshield, manufactured by Rohm and Haas). Polymers may also be solvent-based polymers such as polyamides (e.g. Gental, manufactured by General Plastics) or polyurethane (e.g., Spenlite, manufactured by Reichold Chemicals).

The binder may also comprise a wax material such as microcrystalline wax, polyethylene glycol (PEG) based coatings. A low melting point microcrystalline wax (LMP) mp. about 62–68 C., is preferred.

In conjunction with or independent of the polymer or wax coating, an adhesive may be used such as acrylic adhesives (e.g. Gelva, from Monsanto). These adhesives will provide a tacky surface to which the encapsulated flavors can be adhered.

The flavorants, sweeteners and/or chemotherapeutic agents may typically be encapsulated or formed by spray drying with a material such as starch, cyclodextrins, gum arabic, gum acacia, corn starch, dextrins, ureaformaldehyde or polymethacrylate copolymer, microsponge material such as Polytrap, manufactured by APS, or a waxy material. Waxes may be PEG-type waxes or parafin waxes. The terms "encapsulants" and "encapsulated particles" used in the context of the invention include particles formed by spray drying, although spray dried particles are not typically of a shell-and-core structure.

An important feature of the invention is that the flavorant, sweetener and chemotherapeutic agent are encapsulated together in microparticles in a constant proportion so that there is an even distribution on the floss, that is, there will be no spots in which there is more sweetener than flavorant or more flavorant than sweetener, etc. The adjustment of proportion of flavorant to sweetener is well within the level of skill of those in the art. Typically the proportions by weight will be within 95:5 to 5:95 (flavor: sweetener).

The use of chemotherapeutic agents, such as sodium or stannous fluoride, chlorhexidene and triclosan, is also adjustable as desired. Typical, amounts will be in the range of 90% to 10% by weight of the amount of flavorant which is present.

Typical flavorants are those oils used for mint, spearmint or other similar desirable flavoring. A sweetener will typically be saccharin or other synthetic sweetener.

The present invention provides an advantage in that the consumer experiences a balanced taste of the flavor and sweetener when using encapsulated flavors. If a sweetener is manually mixed with an encapsulated flavor, the taste is not balanced due to uneven distribution of the sweetener resulting in pockets of high and low sweetness. The present invention also eliminates steps of additional application whereby a chemotherapeutic agent must be dissolved in a water-based polymer, suspended in an oil-based composition or dissolved in an emulsion formulation in order to be separately applied to the floss.

To prepare the encapsulated flavors, typically an emulsion is formed using, for example, a water soluble sweetener such as sodium saccharin and a water soluble chemotherapeutic agent, such as sodium fluoride, stannous fluoride or chlorhexidene. The encapsulating material, such as starch, is added with the flavoring oil to form an emulsion. Typically the emulsion has a solids content of 25% to 35% and may be slightly heated to a temperature in the range of about 30–60 C. for improved mixing. This emulsion is then passed through an atomizer, typically heated at the inlet 150–200 C. and the temperature at the outlet will be around 90–110 C. These conditions are typical but may be adjusted according to the ingredients which are used. Upon exit from the outlet, the water evaporates resulting in the formation of a droplet and encapsulation by the starch around a flavor oil core. Residual water continues to evaporate from the droplet. Since the encapsulant, starch in this case, as well as the sodium saccharin or sodium fluoride are water soluble, these latter two agents bond with the starch shell wall and the flavor oil is enclosed within the shell wall. Alternatively, the sweetener may be mixed directly into the flavor oil if it is in an oil soluble form, such as saccharinic acid, and then processed as described above.

The following examples are provided for the purpose of illustration and are not intended to limit the invention in any way.

EXAMPLE 1

The following formulation was prepared:

Microcrystalline wax 43.90% (weight/weight).

Mint flavored TP2850 50.00%

Saccharanic acid 1.10%

Glyceryl Oleate 4.90%

BHT (Butylated hydroxy toluene 0.10%)

This wax was coated onto a bi-component filament yarn composed of nylon BS700 as the core and pebax 2553S sheath in a 70/30 ratio.

EXAMPLE 2

Microcrystalline wax LMP with 20% mineral oil was applied at 5–25% coating level by weight onto a yarn formed from islands of nylon BS700 surrounded by a sea of pebax 2533. This was followed by dusting of spray dried (in starch) mint flavored TP2850 and 1% sodium saccharin. Excess encapsulated material was removed by shaking yarn wiping with tissue, vacuum or airbrush.

EXAMPLE 3

Microcrystalline wax LMP was applied at 5–25% coating level by weight of the yarn identified in example 2, followed by dusting of sprayed dry (with starch) mint flavor TP 2850 and 1% sodium saccharin. Excess capsulate was removed as above.

EXAMPLE 4

Microcrystalline wax LMP with 5% liquid mint flavored oil TP2850was applied at a 5–25% coating level by weight on the yarn identified in example 2, followed by dusting of spray dried (in starch) mint flavor TP 2850and 1% sodium saccharin.

EXAMPLE 5

Samples of the floss described in examples 1and 2were coated with Gelva 2397 (an adhesive from Monsanto Company) using Kimwipe tissues. The solvent was evaporated at room temperature. Encapsulated flavor was dusted on and the excess was removed by gently wiping using a tissue. The adhesive coating weight of about 40–70% was applied and the spray dried (in starch) flavor containing TP2850 with 1% saccharin of 10–15% by weight.

EXAMPLE 6

The gel floss was coated with Gelva 2397 using tissues. The solvent was evaporated at room temperature. Spray dried (in starch) flavor was dusted on and the excess was removed by gently wiping using a tissue. The adhesive coating weight was about 5%. And the spray dry flavor was 5% by weight containing TP 2850 with 1% saccharin.

In all of the above examples the application of the encapsulated material is found to be a suitable means for adhering encapsulated flavors to the surface of dental floss. In all cases the flavored floss was found to release flavor oil upon use but in the oral cavity by means of dissolution or mechanical abrasion of the capsule wall.

What is claimed is:

1. A dental floss comprising:
    a plurality of filaments in a substrate material formed into a thread;
    an ingestible binder on said filaments;
    and particles containing an encapsulated mixture of agents wherein said particles are bound by said binder to said filaments and said agents comprise a sweetener and a flavorant in a predetermined sweetener: flavorant ratio.

2. A floss according to claim 1 wherein said mixture of agents further comprises a chemotherapeutic agent.

3. A floss according to claim 2 wherein said chemotherapeutic agent is selected from the group consisting of sodium fluoride and stannous fluoride.

4. A floss according to claim 1 or 2 wherein said flavorant comprises mint flavor oil.

5. A floss according to claim 1 wherein said sweetener comprises a saccharin derivative.

6. A floss according to claim 5 wherein said sweetener comprises sodium saccharide.

7. A floss according to claim 5 wherein said sweetener comprises saccharinic acid.

8. A floss according to claim 1 wherein said agents are encapsulated in an encapsulant selected in a group consisting of starch, cyclodextrin, ureaformaldehyde, gum arabic, gum acacia, corn starch and dextrins.

9. A floss according to claim 1 wherein said binder comprises a polymer.

10. A floss according to claim 9 wherein said polymer comprises an aqueous-soluble polymer.

11. A floss according to claim 10 wherein said polymer comprises an alkylene vinyl copolymer.

12. A floss according to claim 9 wherein said binder comprises a solvent soluble polymer.

13. A floss according to claim 12 wherein said polymer is selected from the group consisting of polyamide and polyurethane.

14. A floss according to claim 9 wherein said binder comprises a wax.

15. A floss according to claim 14 wherein said wax comprises a low melting point microcrystalline wax.

16. A floss according to claim 9 wherein said binder comprises an adhesive.

* * * * *